(12) United States Patent
Meynial-Salles et al.

(10) Patent No.: US 8,252,579 B2
(45) Date of Patent: Aug. 28, 2012

(54) EVOLVED MICRO-ORGANISMS FOR THE PRODUCTION OF 1,2-PROPANEDIOL

(75) Inventors: Isabelle Meynial-Salles, Fourquevaux (FR); Benjamin Gonzalez, Riom (FR); Philippe Soucaille, Deyme (FR)

(73) Assignee: Metabolic Explorer, Saint Beauzire (FR)

( * ) Notice: Subject to any disclaimer, the term of this patent is extended or adjusted under 35 U.S.C. 154(b) by 542 days.

(21) Appl. No.: 10/585,040

(22) PCT Filed: Jan. 12, 2005

(86) PCT No.: PCT/FR2005/000070
§ 371 (c)(1),
(2), (4) Date: Jul. 18, 2006

(87) PCT Pub. No.: WO2005/073364
PCT Pub. Date: Aug. 11, 2005

(65) Prior Publication Data
US 2007/0072279 A1     Mar. 29, 2007

(30) Foreign Application Priority Data
Jan. 12, 2004   (FR) ..................................... 04 00214

(51) Int. Cl.
*C12Q 1/68*     (2006.01)
*C12P 7/02*     (2006.01)
*C12N 1/20*     (2006.01)
*C12N 9/00*     (2006.01)
*C12N 9/02*     (2006.01)
*C12N 9/04*     (2006.01)
*C12N 15/00*    (2006.01)
*C07H 21/04*    (2006.01)

(52) U.S. Cl. .................... 435/252.33; 435/6.1; 435/155; 435/183; 435/189; 435/190; 435/252.3; 435/320.1; 435/440; 536/23.2

(58) Field of Classification Search .................. None
See application file for complete search history.

(56) References Cited

U.S. PATENT DOCUMENTS
6,303,352 B1 * 10/2001 Cameron et al. .............. 435/158

FOREIGN PATENT DOCUMENTS
WO     WO98/37204     8/1998

OTHER PUBLICATIONS

Bermejo et al. Expression of Clostridium acetobutylicum ATCC 824 genes in *Escherichia coli* for acetone production and acetate detoxification. Appl Environ Microbiol. Mar. 1988;64(3):1079-85.*
Harder et al. A Review Microbial Selection in Continuous Culture. Journal of Applied Bacteriology 1977, 43, 1-24.*
Altaras et al. (1999) *Applied and Environmental Microbiology* 65:1180-1185.
Altaras et al. (2000) *Biotechnol. Prog.* 16:940-946.
Cameron et al. (1988) *Biotechnol. Prog.* 14:116-125.
Girbal et al. (1998) *TIBTECH* 16:11-16.
Snoep et al. (1993) *FEMS Microbiology Letters* 114:279-284.
Stephens et al. (1983) *Eur. J. Biochem.* 135:519-527.
Tran-Din et al. (1985) *Arch. Microbiol.* 142:87-90.

* cited by examiner

*Primary Examiner* — Yong Pak
(74) *Attorney, Agent, or Firm* — Baker, Donelson, Bearman, Caldwell & Berkowitz, PC

(57) ABSTRACT

The present invention concerns a new method of preparation of a strain of evolved micro-organisms for the production of 1,2-propanediol by the metabolism of a simple carbon source, which method comprises the growth under selection pressure in an appropriate growth medium containing a simple carbon source of an initial bacterial strain that has undergone the deletion of the gene tpiA and the deletion of at least one gene involved in the conversion of methylglyoxal (propanal) into lactate, in order to cause, in said initial strain, the evolution of one or more genes involved in the biosynthesis pathway from DHAP to methylglyoxal and then to 1,2-propanediol towards evolved genes that possess an improved "1,2-propanediol synthase activity", the resulting strain or strains of evolved micro-organisms possessing an improved "1,2-propanediol synthase activity" then being selected and isolated.
The invention also concerns the initial micro-organisms and the evolved micro-organisms thus obtained, and a method for the preparation of 1,2-propanediol and possibly acetone by culture of said evolved micro-organisms.

14 Claims, 3 Drawing Sheets

EVOLVED MICRO-ORGANISMS FOR THE PRODUCTION OF 1,2-PROPANEDIOL

This is a U.S. National Stage Application under 35 U.S.C. §371 of International Patent Application No. PCT/FR2005/000070, filed Jan. 12, 2005, which claims priority to French Patent Application No. 0400214, filed Jan. 12, 2004. The contents of both applications are incorporated in their entirety by reference.

The present invention concerns a new method for the preparation of an evolved micro-organism to produce 1,2-propanediol, the evolved micro-organism thereby obtained and its use for the preparation of 1,2-propanediol.

1,2-propanediol or propylene glycol, a C3 dialcohol, is a widely-used chemical. It is a component of unsaturated polyester resins, liquid detergents, coolants, anti-freeze and de-icing fluids for aircraft. Propylene glycol has been increasingly used since 1993-1994 as a replacement for ethylene derivatives, which are recognised as being more toxic than propylene derivatives.

1,2-propanediol is currently produced by chemical means using a propylene oxide hydration process that consumes large amounts of water. Propylene oxide can be produced by either of two processes, one using epichlorhydrin, and the other hydroperoxide. Both routes use highly toxic substances. In addition, the hydroperoxide route generates by-products such as ter-butanol and 1-phenyl ethanol. For the production of propylene to be profitable, a use must be found for these by-products. The chemical route generally produces racemic 1,2-propanediol, whereas each of the two stereoisomers (R)1,2-propanediol and (S)1,2-propanediol are of interest for certain applications.

These disadvantages of the chemical synthesis of 1,2-propanediol make biological production an attractive alternative. Several micro-organisms are able to produce (S) or (R)1,2-propanediol naturally from sugars, such as glucose or xylose, which are metabolised by the glycolysis route, or from deoxyhexoses, which yield (S) 1,2-propanediol (Cameron D. C. et al. (1998) *Biotechnol. Prog.*). The best performing micro-organisms include *Clostridium sphenoides* (Tran Din K. et al. 1986) and *Thermoanaerobium thermosaccharolyticum* (Altaras N. E. & Cameron D. C. 2001). The latter is able to ferment several types of sugars to (R)1,2-propanediol with a yield ranging from 0.13 to 0.28 g of 1,2-propanediol produced per gram of glucose consumed. In these two micro-organisms, the enzymes responsible for the synthesis of 1,2-propanediol have not been identified, and any improvement in their performance is limited by a shortage of available genetic tools. In addition, although *E. coli* does not produce 1,2-propanediol naturally it possesses all the genes necessary for its production. Currently 1,2-propanediol has to be produced from methylglyoxal, a substance that is highly toxic for the cell even at low concentrations. Also, processes using strains of *E. coli* that have been genetically modified to produce 1,2-propanediol have been described, in particular in U.S. Pat. No. 6,303,352, U.S. Pat. No. 6,087,140 and WO 98/37204. These processes use, in particular, the over-expression of one or more of the enzymes involved in the metabolic 1,2-propanediol production route by cloning of their genes in plasmids, and so require a selection pressure using antibiotics. To improve the performance of the strains, certain endogenous genes are also deleted (see for example Altaras N. E. & Cameron D. C. (2000) *Biotechnol. Prog.* 16, 940-946: Altaras N. E. & Cameron D. (1999) *Appl. Env. Microb.*, 65, 1180-1185).

No method using an evolved micro-organism to co-produce 1,2-propanediol and acetone, two useful products, has been described to date.

The present invention concerns a method for the preparation of a strain of an evolved micro-organism for the production of 1,2-propanediol by the metabolism of a simple carbon source, which method comprises the culture, under selection pressure in an appropriate growth medium containing a simple carbon source, of an initial bacterial strain that has undergone deletion of the gene tpiA and the deletion of at least one gene involved in the conversion of methylglyoxal (propanal) into lactate, in order to cause the evolution in said initial strain of one or more genes responsible for the bioconversion of DHAP into methylglyoxal and subsequently into 1,2-propanediol towards modified genes with an improved '1,2-propanediol synthase' activity, which evolved strains of the micro-organism that have said improved '1,2-propanediol synthase' activity are then selected and isolated.

The gene tpiA codes for triose phosphate isomerase, which catalyses the conversion of DHAP into glyceraldehyde 3-phosphate. The purpose of the deletion of this gene is to ensure the synthesis of a sufficient quantity of methylglyoxal. Theoretically, the deletion of the gene tpiA must ensure that 50% of the carbon of the glucose metabolised by the cells is allocated to the preparation of methylglyoxal from dihydroxy acetone phosphate.

The purpose of the deletion of at least one gene involved in the conversion of methylglyoxal (propanal) into lactate is to inhibit the conversion of methylglyoxal into lactate, so that the methylglyoxal present and produced by the initial strain, and by the evolved strain obtained, is used by the cell machinery of said strains essentially for the preparation of 1,2-propanediol.

The genes involved in the conversion of methylglyoxal into lactate can be either the gene gloA coding for glyoxylase I (catalysing the synthesis of lactoyl glutathione from methylglyoxal) or the genes aldA and aldB coding for a lactaldehyde dehydrogenase (catalysing the synthesis of (S) lactate from (S) lactaldehyde). All three genes gloA, aldA and aldB are preferentially deleted in the initial strain.

An additional modification is advantageously made to the initial strain consisting in suppressing the natural glucose fermentation routes, which consume reducing equivalents as NADH, in order to eliminate these metabolic pathways, which compete with 1,2-propanediol production.

In particular, it is advantageous to delete the gene ldhA coding for lactate dehydrogenase catalysing the synthesis of lactate from pyruvate, and the gene adhE coding for alcohol-aldehyde dehydrogenase catalysing the synthesis of ethanol from acetyl-CoA.

Similarly, it is possible to cause the micro-organism to use the pyruvate dehydrogenase complex to produce, anaerobically, acetyl-CoA and NADH from pyruvate. This can be achieved by deleting the genes pflA and pflB coding for pyruvate formate lyase.

In a specific embodiment, the initial strain has thus also undergone the deletion of one or more of the genes ldhA, pflA, pflB and adhE, and preferentially the deletion of all four genes ldhA, pflA, pflB and adhE.

Even more advantageously, the initial strain according to the invention will also contain at least one gene coding for an enzyme favouring the anaerobic metabolism of pyruvate into acetate.

Preferentially, the enzyme favours the anaerobic metabolism of pyruvate towards the production of acetyl-CoA and NADH. More preferentially this enzyme is a pyruvate dehydrogenase complex.

Advantageously, said gene coding for an enzyme favouring the anaerobic metabolism of pyruvate into acetate has reduced sensitivity to inhibition by NADH.

This gene can be an endogenous gene, coding for an endogenous protein, or an exogenous or heterologous gene coding for an endogenous or exogenous enzyme.

In the case of an endogenous gene coding for an endogenous protein sensitive to inhibition by NADH, the evolution process according to the invention makes it possible to select the strains with improved '1,2-propanediol synthase' activity in which said gene coding for an enzyme favouring the anaerobic metabolism of pyruvate into acetate codes for an evolved enzyme that has reduced sensitivity to inhibition by NADH.

According to another embodiment of the invention it is possible to introduce a heterologous gene into the initial strain, which gene codes for an enzyme that has reduced sensitivity to inhibition by NADH, or codes for a sensitive enzyme which, however, is made less sensitive by implementing the evolution process according to the invention.

In addition, it is advantageous also to delete the gene edd coding for 6-phospho-gluconate dehydratase, the first enzyme involved in the Entner-Doudoroff pathway, to prevent the direct metabolism of glucose into glyceraldehyde-3-phosphate and pyruvate and so induce the conversion of glucose into 1,2 propanediol and acetate It is advantageous to introduce, into the previously isolated evolved strain obtained by the evolution process according to the invention, one or more heterologous genes coding for one or more enzymes involved in the conversion of acetyl-CoA and acetate into acetone, to obtain a modified evolved strain.

This new modification makes it possible to produce 1,2-propanediol and acetone, a useful by-product. This modification offers, in addition, the advantage of improving the 1,2-propanediol production performance. Acetate is an inhibitor of the bacterial growth at low concentrations (15 g/l) and rapidly blocks the evolution of the performance of the strain grown chemostatically in anaerobic conditions.

The introduction into the evolved strain of genes coding for the enzymes that catalyse the conversion of acetate into acetone results in a fall in the residual acetate concentration during chemostatic growth. Acetone is produced, which is much less growth-inhibiting than acetate. The growth of the strain and the production of 1,2-propanediol are thus favoured.

Advantageously the heterologous gene or genes coding for one or more enzymes involved in the conversion of acetyl-CoA and acetate come from *C. acetobutylicum*. The genes coding for one or more enzymes involved in the conversion of acetyl-CoA and acetate into acetone can be expressed chromosomically or extrachromosomically. Chromosomically, one or more copies can be introduced into the genome with the help of recombinant methods known to those skilled in the art. Extrachromosomically, the genes can be carried by various types of plasmids that differ in their replication origin, their number of copies and their stability in the cell. They can be present in 1 to 5 copies, or 20 copies or more than 500 copies, corresponding to plasmids with low copy numbers and a strict replication type (pSC101, RK2), plasmids with low copy numbers (pACYC, pRSF1010) or plasmids with high copy numbers (pSK bluescript II). The genes can be expressed using promoters with different strengths, inducible or non-inducible. These can be for example promoters Ptrc, Ptac or Plac, or other promoters known by those skilled in the art. The expression of target genes can be increased or decreased by elements that stabilise or destabilise messenger RNA (Carrier & Keasling (1998) Biotechnol. Prog., 15, 58-64) or proteins (e.g. GSTtags, Amersham Biosciences).

In a preferred embodiment of the invention the previously obtained modified evolved strain is grown under selection pressure in an appropriate growth medium containing a simple carbon source to cause the evolution in said modified evolved strain of one or mores genes involved in the conversion of acetyl-CoA and acetate into acetone towards an improved 'acetone synthase activity'. The second generation of the evolved strains possessing an improved '1,2-propanediol synthase activity' and an improved 'acetone synthase activity' are then selected and isolated.

The present invention also concerns an initial strain according to the invention as described above, below and in the Examples.

It also concerns an evolved strain possessing an improved '1,2-propanediol synthase activity' that can be obtained by the method of the invention as described above, below and in the Examples, including the second generation of evolved strains that additionally possess an 'improved acetone synthase activity'.

Lastly, the invention concerns a method for the preparation of 1,2-propanediol whereby an evolved strain according to the invention is grown in an appropriate growth medium containing a simple carbon source, after which the 1,2-propanediol produced and acetone that may be co-produced are recovered and, if necessary, purified.

The initial modified and evolved strains of micro-organisms according to the invention can be prokaryotes or eukaryotes that can be converted and grown so as to cause them to produce 1,2-propanediol and possibly also acetone.

Those skilled in the art will be able to select said micro-organisms based on general knowledge in cell and molecular biology, and if necessary identify the genes of these micro-organisms that correspond to the genes of *E. coli* mentioned above.

The term 'strain of micro-organisms' according to the invention is taken to denote a set of micro-organisms belonging to the same species that comprises at least one micro-organism of that species. Thus the characteristics described for the strain apply to each of the micro-organisms of that strain. Reciprocally, the characteristics described for any one of the micro-organisms of the strain apply to all the micro-organisms of that strain.

The micro-organisms modified according to the invention can be bacteria, yeasts or fungus, and in particular any of the following species: *Aspergillus* sp., *Bacillus* sp., *Brevibacterium* sp., *Clostridium* sp., *Corynebacterium* sp., *Escherichia* sp., *Gluconobacter* sp., *Pseudomonas* sp., *Rhodococcus* sp., *Saccharomyces* sp., *Streptomyces* sp., *Xanthomonas* sp., *Candida* sp.

In a preferred embodiment, the bacterial strain is a strain of *Escherichia*, in particular of *E. coli*. In another embodiment the bacterial strain is a strain of *Corynebacterium*, in particular *C. glutamicum*.

In another embodiment, the strain of yeast is a strain of *Saccharomyces*, in particular *S. cerevisiae*.

The invention is described above, below and in the Examples in terms of *E. coli*. Thus the genes that can be deleted or over-expressed for the evolved strains according to the invention are defined mainly using the denomination of the gene of *E. coli*. However, this designation has a more general meaning according to the invention, and covers the corresponding genes in other micro-organisms. Using the GenBank references of the genes of *E. coli*, those skilled in the art can determine equivalent genes in bacterial strains other than *E. coli*.

The means of identification of the homologous sequences and their percentage homologies are well-known to those skilled in the art, and include in particular the BLAST programmes that can be used on the website ncbi.nim.nih.gov/BLAST/, with the default parameters indicated on that website. The sequences obtained can be exploited (aligned) using for example the programmes CLUSTALW (ebi.ac.uk/clustalw/) or MULTALIN (prodes.toulouse.inra.fr/multalin/cgi-bin/multalin.pl), with the default parameters indicated on these websites.

Using the references given on GenBank for the genes that are known, those skilled in the art can determine the equivalent genes in other organisms, bacterial strains, yeasts, fungi, mammals and plants, etc. This routine work is advantageously performed using consensus sequences that can be determined using sequence alignments with genes from other micro-organisms, and by designing degenerate probes by means of which the corresponding gene can be cloned in another organism. These routine techniques of molecular biology are well known to the art and are described, for example, in Sambrook et al. (1989 Molecular cloning: a laboratory manual. $2^{nd}$ Ed. Cold Spring Harbor Lab., Cold Spring Harbor, N.Y.).

The term 'deletion' according to the invention denotes the suppression of the activity of a gene, which is then said to be 'deleted'. This suppression of activity can be an inactivation, by an appropriate means, of the product of the expression of the gene concerned, or it can be an inhibition of the expression of the gene concerned, or it can be the deletion of at least a part of the gene concerned so that it is not expressed (for example deletion of all or a part of the promoter region necessary for its expression), or so that the expression product loses its function (for example deletion in a coding part of the gene concerned). Preferentially, the deletion of a gene is essentially the suppression of that gene, which gene can be replaced by a selection marker gene that facilitates the identification, isolation and purification of the evolved strains according to the invention.

A gene is inactivated preferentially by homologous recombination (Datsenko, K. A. & Wanner, B. L. (2000) One-step inactivation of chromosomal genes in *Escherichia coli* K-12 using PCR products. Proc. Natl. Acad. Sci. USA 97: 6640-6645). Briefly, an inactivation protocol can be as follows: a linear fragment of DNA is introduced into the cell. This fragment is obtained in vitro, and comprises the two regions flanking the gene, and at least one selection gene located between these two regions (generally an antibiotic-resistance gene). This fragment thus presents an inactivated gene. The cells that have undergone a recombination event and integrated the fragment introduced are selected by plating on a selective growth medium. The cells that have undergone a double recombination event, in which the native gene has been replaced by the inactivated gene, are then selected. This protocol can be improved using positive and negative selection systems in order to speed up the detection of double recombination events.

The technique preferentially used to introduce these genes into the strain is electroporation, which is well known to those skilled in the art. Briefly, an electroporation protocol can be as follows: the heterologous genes of interest are cloned in an expression vector between a promoter and a terminator. This vector also possesses an antibiotic resistance gene to select cells that contain it and a functional replication origin in the host strain so it can be maintained. The protocol requires the preparation of electrocompetent host cells, which are then converted by electroporation by the vector.

According to the invention, the genes introduced by electroporation are preferentially the genes adc, ctfA and B, thl coding respectively for acetoacetate carboxylase, coenzyme A transferase and the thiolase of the natural acetone production route of *Clostridium acetobutylicum*, a micro-organism recognised as being a very powerful biological producer of acetone.

The evolution process according to the invention is a method for the preparation of evolved micro-organisms whereby it is possible to modify metabolic pathways and which preferentially comprises the following steps:

a) Modification of a micro-organism to obtain an initial micro-organism in such a way as to inhibit the production or consumption of an otherwise produced or consumed metabolite when the cells of the initial micro-organism are grown on a set medium, b) Growth of the initial modified micro-organisms obtained above on said set medium in order to cause it to evolve, where the set medium can also contain a co-substrate necessary for that evolution, c) Selection of the cells of modified micro-organisms able to grow on the set medium, if necessary with an added co-substrate.

An evolution process of this type is described in particular in the patent application WO 04/076659, the contents of which are included herein for reference.

The evolved metabolic route is specifically the 1,2-propanediol synthesis pathway, and when appropriate the acetone synthesis pathway.

The term 'set medium' according to the invention denotes a medium of known molecular composition adapted to the growth of the micro-organism. The set medium is essentially free of metabolite, the production or consumption of which is suppressed by the modification.

The term 'co-substrate' according to the invention denotes a substance that can be organic or inorganic, and that is different from the substrate, that takes part in a reaction in which it gives one or more of its atoms to the substrate to form the end product. The co-substrate has no known mutagenic properties.

The term 'selection' according to the invention denotes a growth process, that can be continuous, that is conducted by applying increasing rates of dilution in such a way as to conserve in the growth medium only those micro-organisms that display a growth rate equal to or higher than the imposed rate of dilution. In this way the micro-organisms conserved are those for which the modification carried out no longer affects growth.

The term 'evolved gene' according to the invention denotes a sequence of nucleic acids bounded by start and stop codons in phase, and which, after selection, differs from the initial sequence by at least one nucleic acid.

The term 'evolved protein' according to the invention denotes a sequence of amino acids (protein sequence) which, after selection, differs from the initial sequence by at least one amino acid.

The genes and proteins can be identified by their primary sequences, and also by sequence homologies or alignments that define groups of proteins.

The PFAM database (protein families database of alignments and hidden Markov models, sanger.ac.uk/Software/Pfam/) is a large collection of alignments of protein sequences. Each PFAM makes it possible to visualise multiple alignments, view protein domains, evaluate distributions among organisms, gain access to other databases and visualise known protein structures.

COGs (clusters of orthologous groups of proteins, ncbi.nlm.nih.gov/COG/) are obtained by comparing protein sequences derived from 43 fully sequenced genomes representing 30 major phylogenetic lines. Each COG is defined from at least three lines, making it possible to identify ancient conserved domains.

According to the invention the terms 'culture', 'growth' and 'fermentation' are used interchangeably to denote the growth of bacteria on an appropriate growth medium containing a simple carbon source.

The term 'simple carbon source' according to the present invention denotes any source of carbon that can be used by those skilled in the art to support the normal growth of a micro-organism and in particular of bacteria, and which can be arabinose, fructose, galactose, glucose, lactose, maltose, sucrose or xylose. An especially preferred simple carbon source is glucose.

The culture conditions for the micro-organisms according to the invention (fermentation) can be readily defined by those skilled in the art. In particular, bacteria are fermented at temperatures between 20° C. and 55° C., preferably between 25° C. and 40° C., and preferably at about 30° C. for *C. glutamicum* and *S. cerevisiae* and at about 34° C. for *E. coli*.

The fermentation is generally conducted in fermenters with a mineral culture medium of known set composition adapted to the bacteria used, containing at least one simple carbon source and, if required, a cofactor necessary for the production of the metabolite.

In particular, the mineral growth medium for *E. coli* can thus be of identical or similar composition to M9 medium (Anderson, 1946, *Proc. Natl. Acad. Sci.* USA 32:120-128), M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as that defined by Schaefer et al. (1999, *Anal. Biochem.* 270: 88-96), and in particular the minimum culture medium described below:

| | |
|---|---|
| $K_2HPO_4$ | 1 g/l |
| N.T.A | 0.2 g/l |
| trace element solution* | 10 ml/l |
| $(NH_4)_2SO_4$ | 1 g/l |
| NaCl | 0.2 g/l |
| $NaHCO_3$ | 0.2 g/l |
| $MgSO_4$ | 0.2 g/l |
| glucose | 20 to 100 g/l |
| sodium nitrate | 0.424 g/l |
| thiamine | 10 mg/l |
| $FeSO_4$ | 50 mg/l |
| yeast extract | 4 g/l |
| spectinomycin | 100 mg/l |

The pH of the medium is adjusted to 7.4 with sodium hydroxide.
*trace element solution: Citric acid 4 g/L, $MnSO_4$ 3 g/L, NaCl 1 g/L, $CoCl_2$ 0.1 g/L, $ZnSO_4$ 0.10 g/L, $CuSO_4$ 10 mg/L, $H_3BO_3$ 10 mg/L, $NaMoO_4$ 10 mg/L.
Analogously, the mineral growth medium for *C. glutamicum* can also be of identical or similar composition to BMCG medium (Liebl et al., 1989, *Appl. Microbiol. Biotechnol.* 32: 205-210) or to a medium such as that defined by Riedel et al. (2001, *J. Mol. Microbiol. Biotechnol.* 3: 573-583).

The fermentation is preferentially conducted anaerobically and chemostatically, i.e. fed continuously, at a fixed dilution rate, the said minimum growth medium containing a fixed concentration of a carbon source and degassed with nitrogen.

The concentration of the carbon source in the fermentation feed medium is increased only once a permanent regimen limited by the residual carbon source concentration is reached and has remained stable for several days.

The preferred culture mode is the chemostatic culture mode, because it favours improved growth and 1,2-propanediol production performance by the modified strain and allows the isolation of the evolved micro-organisms.

The term improved '1,2-propanediol synthase activity' according to the invention refers to the improvement of all the enzyme activities involved in the conversion pathway of DHAP into 1,2-propanediol. The improved enzyme activity in the evolved micro-organism results in an increase in the quantity of 1,2-propanediol produced by the evolved micro-organism relative to the quantities produced by the corresponding initial micro-organism in identical culture conditions.

The term improved 'acetone synthase activity' according to the invention refers to the improvement of all the enzyme activities involved in the conversion pathway of acetate and acetyl-CoA into acetone. The evolved enzyme activity in the second-generation evolved micro-organism results in an increase in the amount of acetone produced by the second-generation evolved micro-organism relative to the corresponding modified evolved micro-organism in identical culture conditions.

The invention also concerns the isolation and characterisation of evolved genes in evolved strains obtained by the process according to the invention, and the evolved proteins coded by said evolved genes. These evolved genes can then be introduced into a host organism under the control of appropriate regulation elements for its expression in said organism for the production of the corresponding evolved protein.

The improvement of the performance of the evolved micro-organisms, in particular of the strain *E. coli* MG16555 Δ tpiA, ΔpflAB, ΔadhE, ldhA::kana, ΔgloA, ΔaldA, ΔaldB in the course of chemostatic culture suggests that these growth conditions make it possible to select a functional endogenous pyruvate dehydrogenase complex in anaerobic conditions, in which conditions NADH is abundantly produced. It is known that the pyruvate dehydrogenase complex that catalyses the conversion of pyruvate into acetyl-CoA with release of NADH only functions in aerobic conditions, whereas in anaerobic conditions the pyruvate formate lyase is functional, catalysing the conversion of pyruvate into acetyl-CoA and formate (Snoep J. L., De Graef M. R., Westphal A. H., De Kok A. Teixeira de Mattos M. J. and Neijssel O. M. (1993)). One of the modifications carried out on the modified strain of *E. coli* constructed for the production of 1,2-propanediol, to produce NADH by decarboxylation of pyruvate, is the deletion of the genes pflA and pflB coding for the pyruvate formate lyase activity. The only possibility for the modified cell is to metabolise the pyruvate into acetyl-CoA by means of the pyruvate dehydrogenase complex with production of one NADH equivalent. The pyruvate dehydrogenase complex of the modified evolved strain has been characterised and is less sensitive to NADH than the pyruvate dehydrogenase complex of the wild strain.

The present invention makes possible the selection of a pyruvate dehydrogenase complex that is functional in anaerobic conditions and that produces two NADH equivalents by oxidation of glyceraldehyde-3-phosphate to acetate. These NADH equivalents can be re-oxidised only by the pathway of reduction of dihydroxyacetone-phosphate to 1,2-propanediol. The selection of an enzyme complex with low sensitivity to NADH favours a high rate of production of 1,2-propanediol.

The present invention leads advantageously to the selection of mutations of the gene lpd (the wild sequence of which is known: genolist.pasteur.fr/Colibri) coding for the lipoamide dehydrogenase of the pyruvate dehydrogenase complex. In particular, the presence of a point mutation causing the replacement of alanine 55 by a valine has been identified. This enzyme is known to be responsible for the inhibition of the pyruvate dehydrogenase complex by NADH. This modified enzyme is also an object of the present invention.

The present invention permits the improvement of the performance of the modified micro-organisms, in particular of the strain E. coli MG1655 Δ tpiA, ΔpflAB, ΔadhE, ldhA::kana, ΔgloA, ΔaldA, ΔaldB and also, by evolution in the course of anaerobic chemostatic culture, of the endogenous enzymes involved in the conversion pathway of DHAP into 1,2-propanediol. The evolution of these enzymes results in an increased growth rate and a higher final concentration of 1,2-propanediol.

Preferentially, according to the invention, the evolved strain does not include the evolution of the gene gldA. In a specific embodiment, the gene gldA is deleted in the evolved strain.

Figure 1:
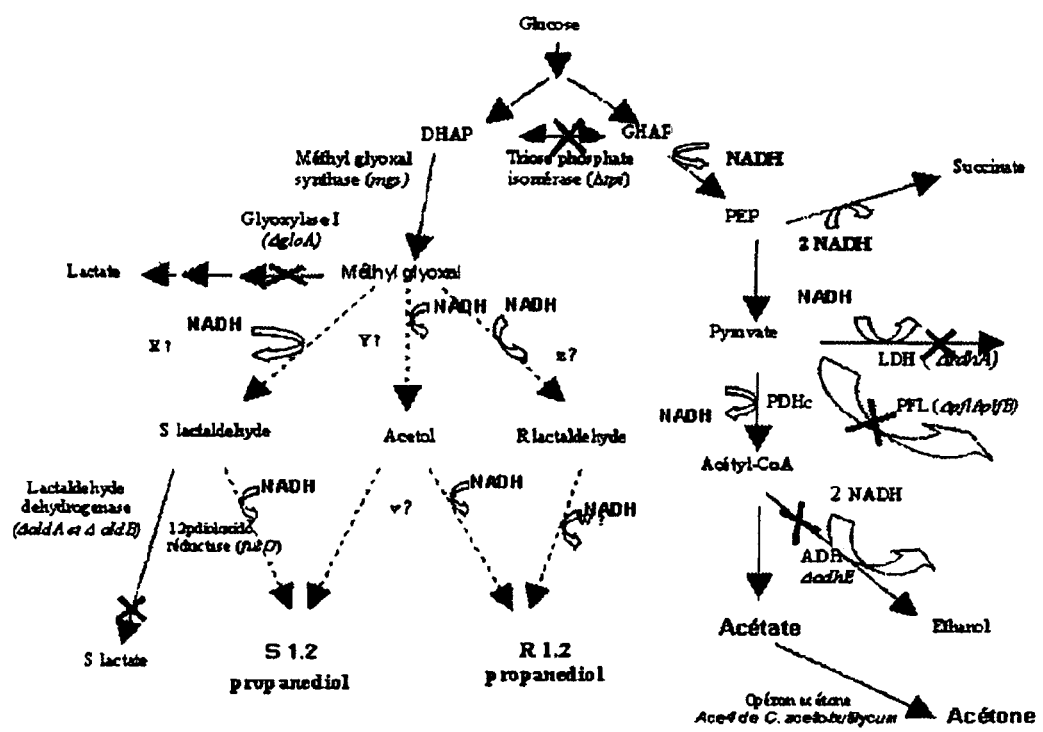
FIG. 1: Diagram of the metabolism of the strain of E. coli modified for the production of 1,2-propanediol and acetone according to the invention Captions:
LDH: lactate dehydrogenase
ADH: aldehyde-alcohol dehydrogenase
PFL: pyruvate formate lyase
PDHc: pyruvate dehydrogenase complex

The examples of embodiments given below are intended to illustrate the invention, and do not limit its scope.

EXAMPLE 1

Construction of a Modified Strain of E. Coil MG1655ΔtpiA, ΔpflAB, ΔadhE, ldhA::kana, ΔgloA, ΔaldA, ΔaldB Able to Produce Only 1,2-propanediol and Acetate by Fermentation of Glucose a) Construction of a Modified Strain E. coli MG1655Δ tpiA::cm The gene tpiA was inactivated by inserting a chloramphenicol antibiotic resistance cassette and deleting most of the gene concerned. The technique used is described by Datsenko, K. A. & Wanner, B. L. (2000) One-step inactivation of chromosomal genes in Escherichia coli K-12 using PCR products. Proc. Natl. Acad. Sci. USA 97: 6640-6645.

Two oligonucleotides were used to replace the gene tpiA:
1. DtpiAr, consisting of 100 bases (SEQ ID NO 1):

atgcgacatcctttagtgatgggtaactggaaactgaacggcagccgcca catggttcacgagctggtttctaacctgcgtaCATATGAATATCCTCCTT

AG with:
a region (lower-case letters) homologous to the sequence (4109007-4109087) of the gene tpiA (sequence 4108320 to 4109087), a reference sequence on the website genolist.pasteur.fr/Colibri/, and a region (upper-case letters) for the amplification of the chloramphenicol resistance cassette of the plasmid pKD3 (Datsenko, K. A. & Wanner, B. L. (2000) One-step inactivation of chromosomal genes in Escherichia coli K-12 using PCR products. Proc. Natl. Acad. Sci. USA 97: 6640-6645).

2. DtpiAf, consisting of 100 bases (SEQ ID NO 2):

cttaagcctgtttagccgcttctgcagctttaacgattactgcgaaggcg tcagctttcagagaagcaccaccaaccagcTGTAGGCTGGAGCTGCTTCG with:
a region (lower-case letters) homologous to the sequence (4108320-4108400) of the tpiA, and
a region (upper-case letters) for the amplification of the chloramphenicol resistance cassette carried by the plasmid pKD3.

The oligonucleotides DtpiAr and DtpiAf were used to amplify the chloramphenicol resistance cassette from the plasmid pKD3. The PCR product obtained was then introduced by electroporation into the strain MG1655 (pKD46) in which the system λ Red (γ, β, exo) expressed greatly favours homologous recombination. The antibiotic-resistant transformants were then selected and the insertion of the resistance cassette was checked by PCR analysis with the oligonucleotides cdh and YllQ.

cdh (SEQ ID NO 3):
ggtgatgatagttatcgccg (homologous to the sequence from 4107536 to 4107555)

YllQ (SEQ ID NO 4):
cgtgccatcgacagcagtcc (homologous to the sequence from 4109599 to 4109580)

The chloramphenicol resistance cassette was then eliminated. The plasmid pCP20 carrying FLP recombinase acting at the FRT sites of the chloramphenicol resistance cassette was then introduced into the recombinant strains by electroporation (Cheperanov P. P. & Wackernagel W. (1995) Gene disruption in Escherichia coli. Tc$^R$ and Km$^R$ cassettes with option of Flp-catalyzed excision of the antibiotic-resistance determinant, gene, 158, 9-14). After serial culture at 42° C., the loss of the antibiotic resistance cassette was checked by PCR analysis with the same oligonucleotides as previously used.

b) Construction of a Modified Strain of E. coli MG1655 ΔplfAB::cm

The genes plfA and pflB were inactivated by inserting a chloramphenicol antibiotic resistance cassette and deleting most of the genes concerned. The technique used is described by Datsenko, K. A. & Wanner, B. L. (2000).

Two oligonucleotides were used to replace the genes pflA and pflB:
1. DplfB r, consisting of 100 bases (SEQ ID NO 5):

ccggacatcctgcgttgccgtaaatctggtgttctgaccggtctgccaga tgcatatggccgtggccgtatcatcggtgaCATATGAATATCCTCCTTAG with:
a region (lower-case letters) homologous to the sequence (952235-952315) of the gene plfB (sequence 950495 to 952777), a reference sequence on the website genolist.pasteur.fr/Colibri/, and
a region (upper case letters) for the amplification of the chloramphenicol resistance cassette of the plasmid pKD3 (Datsenko, K. A. & Wanner, B. L. (2000) One-step inactivation of chromosomal genes in *Escherichia coli* K-12 using PCR products. *Proc. Natl. Acad. Sci. USA* 97: 6640-6645)

2. DplfAf, consisting of 100 bases (SEQ ID NO 6):

gatgcactataagatgtgttaaaaacgctgtagcagaatgaagcgcggaa taaaaaagcggcaactcaataaagttgccgCTGGAGCTGCTTCG with:
- a region (lower-case letters) homologous to the sequence (949470-949550) located above the gene pflA (sequence from 949563 to 950303), and
- a region (upper-case letters) for the amplification of the chloramphenicol resistance cassette carried by the plasmid pKD3.

The oligonucleotides pflAB1 and pflAB2 were used to amplify the chloramphenicol resistance cassette from the plasmid pKD3. The PCR product obtained was then introduced by electroporation into the strain MG1655 (pKD46) in which the expressed enzyme Red recombinase permits the homologous recombination. The antibiotic-resistant transformants were then selected and the insertion of the resistance cassette was checked by PCR analysis with the oligonucleotides pflAB1 and pflAB2.

pflAB 1 (SEQ ID NO 7):
agacattaaaaatatacgtgcagctacccg (homologous to the sequence from 948462 to 948491).

pflAB 2 (SEQ ID NO 8):
gtgaaagctgacaaccctttttgatcttta (homologous to the sequence from 953660 to 983689).

c) Construction of a Modified Strain of *E. coli* MG1655 ΔtpiA, ΔplfAB

The deletion of the genes pflA and pflb by replacement of the genes by a chloramphenicol resistance cassette in the strain MG1655 ΔtpiA was performed by the technique of transduction with phage P1. The protocol was in two steps, (i) the preparation of the phage lysate on the strain MG1655 ΔplfAB::cm and (ii) the transduction of the strain MG1655 ΔtpiA by this phage lysate.

Preparation of the Phage Lysate
  Seeding with 100 μl of an overnight culture of the strain MG1655 (ΔplfAB::cm) of 10 ml of LB+Cm 30 μg/ml+ glucose 0.2%+CaCl$_2$ 5 mM.
  Incubation for 30 min at 37° C. with shaking.
  Addition of 100 μl of phage lysate P1 prepared on the wild strain MG1655 (approx. 1×10$^9$ phage/ml).
  Shaking at 37° C. for 3 hours until all cells were lysed.
  Addition of 200 μl of chloroform, and vortexing.
  Centrifugation for 10 min at 4500 g to eliminate cell debris.
  Transfer of supernatant in a sterile tube and addition of 200 μl of chloroform.
  Storage of the lysate at 4° C.
Transduction
  Centrifugation for 10 min at 1500 g of 5 ml of an overnight culture of the strain MG1655 (ΔtpiA) in LB medium.
  Suspension of the cell pellet in 2.5 ml of MgSO$_4$ 10 mM, CaCl$_2$ 5 mM.
  Control tubes: 100 μl cells
  100 μl phages P1 of the strain MG1655 (ΔpflAB::cm).
  Tube test: 100 μl of cells+100 μl phages P1 of strain MG1655 (ΔpflAB::cm).
  Incubation for 30 min at 30° C. without shaking.
  Addition of 100 μl sodium citrate 1 M in each tube, and vortexing.
  Addition of 1 ml of LB.
  Incubation for 1 hour at 37° C. with shaking
  Plating on dishes LB+Cm 30 μg/ml after centrifugation of tubes for 3 min at 7000 rpm.
  Incubation at 37° C. overnight.
Verification of the Strain The antibiotic-resistant transformants were then selected and the insertion of the containing region (pflAB::cm) was checked by a PCR analysis with (i) the oligonucleotides pflAB1 and pflAB2, and (ii) cdh and YllQ, in order also to check the deletion of the gene tpiA in the strain ΔpflAB::cm. The resulting strain was named MG1655 Δ(pflAB::cm, ΔtpiA).

As above, the chloramphenicol-resistance cassette was then eliminated. The plasmid pCP20 carrying the FLP recombinase acting at the FRT sites of the chloramphenicol resistance cassette was then introduced into the recombinant strains by electroporation. After serial culture at 42° C., the loss of the antibiotic resistance cassette was checked by PCR analysis with the same oligonucleotides as those used previously. The strain obtained was named MG16555 Δ tpiA, ΔpflAB.

d) Construction of a Modified Strain of *E. coli* MG1655 ΔadhE::cm

As previously the gene adhE was inactivated by inserting a chloramphenicol antibiotic resistance cassette and deleting most of the gene concerned using the technique described by Datsenko, K. A. & Wanner, B. L. (2000).

Two oligonucleotides were used to carry out the deletion:
1. DadhE r, consisting of 100 bases (SEQ ID NO 9):

atggctgttactaatgtcgctgaacttaacgcactcgtagagcgtgtaaa aaaagcccagcgtgaatatgccagtttcactCATATGAATATCCTCCTTA

G with:
- a region (lower case letters) homologous to the sequence (1297263-1297343) of the gene adhE (sequence 1294669 to 1297344), a reference sequence on the site genolist.pasteur.fr/Colibri/, and
- a region (upper case letters) for the amplification of the chloramphenicol resistance cassette of the plasmid pKD3 (Datsenko, K. A. & Wanner, B. L. (2000).

2. DadhEf, consisting of 100 bases (SEQ ID NO 10):

caataacgaatgatagcaattttaagtagttaggaggtgaaaaatgctgt caaaaggcgtattgtcagcgcgtcttttcaTGTAGGCTGGAGCTGCTTCG with:
- a region (lower case letters) homologous to the sequence (1294694-1294774) of the gene adhE, and
- a region (upper case letters) for the amplification of the chloramphenicol resistance cassette carried by the plasmid pKD3.

The oligonucleotides DadhEr and DadhEf were used to amplify the chloramphenicol resistance cassette from the plasmid pKD3. The PCR product obtained was then introduced by electroporation into the strain MG1655 (pKD46) in which the expressed enzyme Red recombinase permits homologous recombination. The antibiotic-resistant transformants were then selected, and the insertion of the resistance cassette was checked by PCR analysis with the oligonucleotides ychGf and adhECr.

ychGf (SEQ ID NO 11):
ggctcattgcaccaccatccag (homologous to the sequence from 1294357 to 1294378)

adhECr (SEQ ID NO 12):
gaaaagacgcgctgacaatacgcc (homologous to the sequence from 1297772 to 1297749).

e) Construction of a Strain MG1655 ΔtpiA, ΔpflAB, ΔadhE

The deletion of the gene adhE in the strain MG1655 ΔtpiA, ΔplfAB was performed as previously using the transduction technique with phage P1 (see protocol c). The lysate of phage P1 was obtained on the strain MG1655 ΔadhE::cm, and the transduction of the strain MG1655 ΔtpiAΔpflAB was carried out using this lysate. The chloramphenicol-resistant transductants were verified using the oligonucleotides ychCf and adhECr to check the mutation of the gene adhE and also using (i) the oligonucleotides pflAB1 and pflAB2 and (ii) cdh and YllQ in order also to check the deletion of the genes pflA and B, and tpiA in the strain ΔadhE::cm.

As previously, the chloramphenicol resistance cassette was then eliminated. The plasmid pCP20 carrying the FLP recombinase acting at the FRT sites of the chloramphenicol resistance cassette was then introduced into the recombinant strains by electroporation. After serial culture at 42° C., the loss of the antibiotic resistance cassette was checked by PCR analysis with the same oligonucleotides as used previously. The strain obtained was named MG16555 ΔtpiA, ΔpflAB, ΔadhE.

f) Construction of a Modified Strain of *E. coli* MG1655 ΔtpiA, ΔpflAB, ΔadhE, ldhA::kana The gene ldhA (coordinates 1439878 to 1440867) in the strain MG1655 ΔtpiA, ΔpflAB, ΔadhE was inactivated as above using the phage P1 technique (see protocol c). The phage lysate was obtained with the strain *E. coli* K12 NZN11 Δplf::cam, ldhA::kana supplied by Clark D. P. (Bunch P. K., Mat-Jan F. and Clark D. P. (1997) The ldhA gene encoding the fermentative lactate dehydrogenase of *Escherichia coli* Microbiology, 143, 187-195.). The transduction of the strain MG1655 ΔtpiA, ΔpflAB, ΔadhE was carried out using the phage lysate of the strain *E. coli* K12 NZN11 Δplf::cam, ldhA::kana. The transductants were selected on kanamycin and the insertion of the kanamycin cassette in the gene ldhA was checked using the oligonucleotides hslJC and ldhAC2.

hslJC (SEQ ID NO 13):
gccatcagcaggcttagccg (homologous to the sequence 1439345 to 1439767)

ldhAC2 (SEQ ID NO 14):
gggtattgtggcatgtttaaccg (homologous to the sequence 1441007 to 1441029)

The strain obtained was named MG1655 ΔtpiA, ΔpflAB, ΔadhE, ldhA::kana.

g) Construction of a Modified Strain of *E. coli* MG1655 ΔgloA::cm

The gene gloA was inactivated as above by inserting a chloramphenicol antibiotic resistance cassette and deleting most of the genes concerned using the technique described by Datsenko, K. A. & Wanner, B. L. (2000).

Two oligonucleotides were used to carry out the deletion:
1. GLOAD f, consisting of 100 bases (SEQ ID NO 15)

atgcgtcttcttcataccatgctgcgcgttggcgatttgcaacgctccat cgattttataccaaagtgctgggcatgaaGTGTAGGCTGGAGCTGCTTC

G with:
a region (lower case letters) homologous to the sequence (1725861-1725941) of the gene gloA (sequence 1725861 to 1726268), reference sequence on the website genolist.pasteur.fr/Colibri/, and
a region (upper case letters) for the amplification of the chloramphenicol resistance cassette of the plasmid pKD3 (Datsenko, K. A. & Wanner, B. L. (2000).

2. GLOA D R (SEQ ID NO 16):

ttagttgcccagaccgcgaccggcgtctttctcttcgattaactcaattt tgtaaccgtccggatcttccacaaacgcgaCATATGAATATCCTCCTTAG a region (lower case letters) homologous to the sequence (1726188-1726268) of the gene gloA (1725861-1726268), and
a region (upper case letters) for the amplification of the chloramphenicol resistance cassette carried by the plasmid pKD3.

The oligonucleotides GLOADr and GLOADf were used to amplify the chloramphenicol resistance cassette form the plasmid pKD3. The PCR product obtained was then introduced by electroporation into the strain MG1655 (pKD46) in which the expressed enzyme Red recombinase permits homologous recombination. The antibiotic-resistant transformants were then selected and the insertion of the resistance cassette was checked by PCR analysis with oligonucleotides Nem A C d and Rnt C r.

NemAQd (SEQ ID NO 17):
gaagtggtcgatgccgggattgaagaatggg (homologous from 1725331 to 1725361)

Rnt Cr (SEQ ID NO 18):
gggttacgtttcagtgaggcgcgttctgcgg (homologous to the sequence from 1726765 to 1726795)

h) Construction of a Modified Strain of *E. coli* MG1655 ΔtpiA, ΔpflAB, ΔadhE, ldhA::kana, ΔgloA The gene gloA in the strain MG1655 ΔtpiA, ΔpflAB, ΔadhE, ldhA::kana was inactivated as above using the phage P1 technique (see protocol c). The lysate of the phage P1 was obtained of the strain MG1655 ΔgloA::cm, and the transduction of the strain MG1655 ΔtpiA, ΔpflAB, ΔadhE, ldhA::kana was carried out using this lysate. The chloramphenicol-resistant transductants were verified using the oligonucleotides NemAQd and Rnt Cr to check the mutation of the gene gloA and also using the oligonucleotides pflAB1 and pflAB2, cdh and YllQ, ychCf and adhECr, and hslJC and ldhAC2 in order also to check the deletion of the genes pflA and B, tpiA, adhE, and ldhA in the strain ΔgloA::cm.

As above, the chloramphenicol resistance cassette was then eliminated. The plasmid pCP20 carrying the FLP recombinase acting at the FRT sites of the chloramphenicol resistance cassette was then introduced into the recombinant strains by electroporation. After serial cultures at 42° C., the loss of the cassette was checked by a PCR analysis with the same oligonucleotides as those used previously. The strain obtained was named MG16555 ΔtpiA, ΔpflAB, ΔadhE, ldhA::kana, ΔgloA.

i) Construction of a Modified Strain of *E. coli* MG1655 ΔaldA::cm

The gene aldA was inactivated as above by inserting a chloramphenicol antibiotic resistance cassette and deleting most of the genes concerned using the technique described by Datsenko, K. A. & Wanner, B. L. (2000).

Two oligonucleotides were used to carry out the deletion:
1. AldA D f, consisting of 100 bases (SEQ ID NO 19):

```
atgtcagtacccgttcaacatcctatgtatatcgatggacagtttgttac
ctggcgtggagacgcatggattgatgtggtaGTGTAGGCTGGAGCTGCTT
CG
``` with:
- a region (lower case letters) homologous to the sequence (1486256-1486336) of the gene aldA (sequence 1486256 to 1487695), reference sequence on the website genolist.pasteur.fr/Colibri/, and
- a region (upper case letters) for the amplification of the chloramphenicol resistance cassette of the plasmid pKD3 (Datsenko, K. A. & Wanner, B. L. (2000)

2. aldAD r, consisting of 100 bases (SEQ ID NO 20):

```
ttaagactgtaaataaaccacctgggtctgcagatattcatgcaagccat
gtttaccatctgcgccgccaataccggatttCATATGAATATCCTCCTTA
G
```

- a region (lower case letters) homologous to the sequence (1487615-1487695) of the aldA (1486256 to 1487695).
- a region (upper case letters) for the amplification of the chloramphenicol resistance cassette carried by the plasmid pKD3.

The oligonucleotides AldA D r and aldAD f were used to amplify the chloramphenicol resistance cassette from the plasmid pKD3. The PCR product obtained was then introduced by electroporation into the strain MG1655 (pKD46) in which the expressed enzyme Red recombinase permits homologous recombination. The antibiotic-resistant transformants were then selected and the insertion of the chloramphenicol resistance cassette was checked by PCR analysis with the oligonucleotides Ydc F C f and gapCCr.

Ydc F C f (SEQ ID NO 21):
tgcagcggcgcacgatggcgacgttccgccg (homologous from 1485722 to 1485752)

gapCCr (SEQ ID NO 22):
cacgatgacgaccattcatgcctatactggc (homologous to the sequence from 1488195 to 1488225)

h) Construction of a Modified Strain of *E. coli* MG1655 ΔtpiA, ΔpflAB, ΔadhE, ldhA::kana, ΔgloA, ΔaldA The gene aldA of the strain MG1655 ΔtpiA, ΔpflAB, ΔadhE, ldhA::kana, ΔgloA was inactivated as above using the phage P1 technique (see protocol c). The phage P1 lysate was obtained on the strain MG1655 ΔaldA::cm, and the transduction of the strain MG1655 ΔtpiA, ΔpflAB, ΔadhE, ldhA::kana, ΔgloA was carried out using this lysate. The chloramphenicol-resistant transductants were verified using the oligonucleotides Ydc F C f and gapCCr to check the mutation of the gene aldA and also using the oligonucleotides NemAQd and Rnt Cr, pflAB1 and pflAB2, cdh and YllQ, ychcf and adhECr, and hslJC and ldhAC2 in order also to check the deletion of the genes gloA, pflA and B, tpiA, adhE, respectively, in the strain ΔaldA::cm.

As above, the chloramphenicol resistance cassette was then eliminated. The plasmid pCP20 carrying the FLP recombinase acting at the FRT sites of the chloramphenicol resistance cassette was then introduced into the recombinant strains by electroporation. After serial cultures at 42° C., the loss of the antibiotic resistance cassette was checked by PCR analysis with the same oligonucleotides as those used previously. The strain obtained was named MG16555 Δ tpiA, ΔpflAB, ΔadhE, ldhA::kana, ΔgloA, ΔaldA.

g) Construction of a Modified Strain of *E. coli* MG 1655 ΔaldB::cm

The gene aldB was inactivated as above by inserting a chloramphenicol antibiotic resistance cassette and deleting most of the genes concerned using the technique described by Datsenko, K. A. & Wanner, B. L. (2000).

Two oligonucleotides were used to carry out the deletion:
1. AldB D f, consisting of 100 bases (SEQ ID NO 23)

```
tcagaacagccccaacggtttatccgagtagctcaccagcaggcacttgg
tttgctggtaatgctccagcatcatcttgtGTGTAGGCTGGAGCTGCTTC
G
``` with:
- a region (lower case letters) homologous to the sequence (3752603-3752683) of the gene aldB (sequence from 3752603 to 3754141), reference sequence on the website genolist.pasteur.fr/Colibri/, and
- a region (upper case letters) for the amplification of the chloramphenicol resistance cassette of the plasmid pKD3 (Datsenko, K. A. & Wanner, B. L. (2000)

2. aldBD r, consisting of 100 bases (SEQ ID N°24):

```
atgaccaataatcccccttcagcacagattaagcccggcgagtatggttt
cccctcaagttaaaagcccgctatgacaaCATATGAATATCCTCCTTAG
``` with:
- a region (lower case letters) homologous to the sequence (3754061-3754141) of the gene aldB (3752603 to 3754141), and
- a region (upper case letters) for the amplification of the chloramphenicol resistance cassette carried by the plasmid pKD3.

The oligonucleotides AldB D r and aldB D f were used to amplify the chloramphenicol resistance cassette from the plasmid pKD3. The PCR product obtained is then introduced by electroporation into the strain MG1655 (pKD46) in which the expressed enzyme Red recombinase permits homologous recombination. The antibiotic-resistant transformants were then selected and the insertion of the chloramphenicol resistance cassette was checked by PCR analysis using the oligonucleotides aldB C f and YiaYCr.

aldB C f (SEQ ID NO 25):
catatttccctcaaagaatataaaaaagaacaattaacgc (homologous to the sequence from 3752057 to 3752095)

YiaYCr (SEQ ID NO 26):
tatgttcatgcgatggcgcaccagctgggcg (homologous to the sequence from 3754644 to 3754674)

h) Construction of a Modified Strain of *E. coli* MG1655 ΔtpiA, ΔpflAB, ΔadhE, ldhA::kana, ΔgloA, ΔaldA, ΔaldB The gene aldB in the strain MG1655 ΔtpiA, ΔpflAB, ΔadhE, ldhA::kana, ΔgloA, aldA was inactivated as above using the phage P1 technique (see protocol c). The phage P1 lysate was obtained on the strain MG1655 ΔaldB::cm, and the transduction of the strain MG1655 ΔtpiA, ΔpflAB, ΔadhE, ldhA::kana, ΔgloA, ΔaldA was carried out using this lysate. The chloramphenicol-resistant transductants were verified using the oligonucleotides aldB C f and YiaYCr to check the mutation of the gene aldB and also using the oligonucleotides NemAQd and Rnt Cr, pflAB1 and pflAB2, cdh and YllQ, ychcf and adhECr, hslJC and ldhAC2, and Ydc F C f and gapCCr in order also to check the deletion of the genes gloA, pflA and B, tpiA, adhE, aldA, respectively, in the strain ΔaldB::cm.

As above, the chloramphenicol resistance cassette was then eliminated. The plasmid pCP20 carrying the FLP recombinase acting at the FRT sites of the chloramphenicol resistance cassette was then introduced into the recombinant strains by electroporation. After serial cultures at 42° C., the loss of the antibiotic resistance cassette was checked by PCR analysis with the same oligonucleotides as those used above. The strain obtained was named MG1655 ΔtpiA, ΔpflAB, ΔadhE, ldhA::kana, ΔgloA, ΔaldA, ΔaldB.

EXAMPLE 2

Culture and Evolution of the Modified Strain E. coli MG1655 Δ tpiA, ΔpflAB, ΔadhE, ldhA::kana, ΔgloA, ΔaldA, aldB in Chemostatic Culture To optimise the production of 1,2-propanediol from glucose by the strain E. coli MG1655 Δ tpiA, ΔpflAB, ΔadhE, ldhA::kana, ΔgloA, ΔaldA, ΔaldB, a chemostatic culture of the strain in a minimal culture medium supplemented with sodium nitrate and yeast extract was carried out for several weeks in anaerobic conditions.

Figure 2:
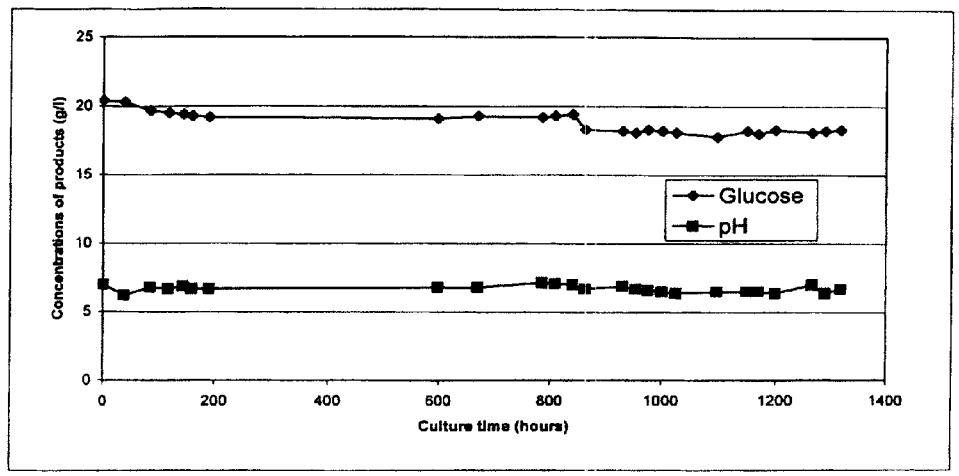
FIG. 2: Evolution of the strain of E. coli MG1655 ΔtpiA, ΔpflAB, ΔadhE, ldhA::kana, ΔgloA, ΔaldA, ΔaldB during chemostatic growth on glucose: concentration of glucose (FIG. 2A and other substances (FIG. 2B).
Figure 2:
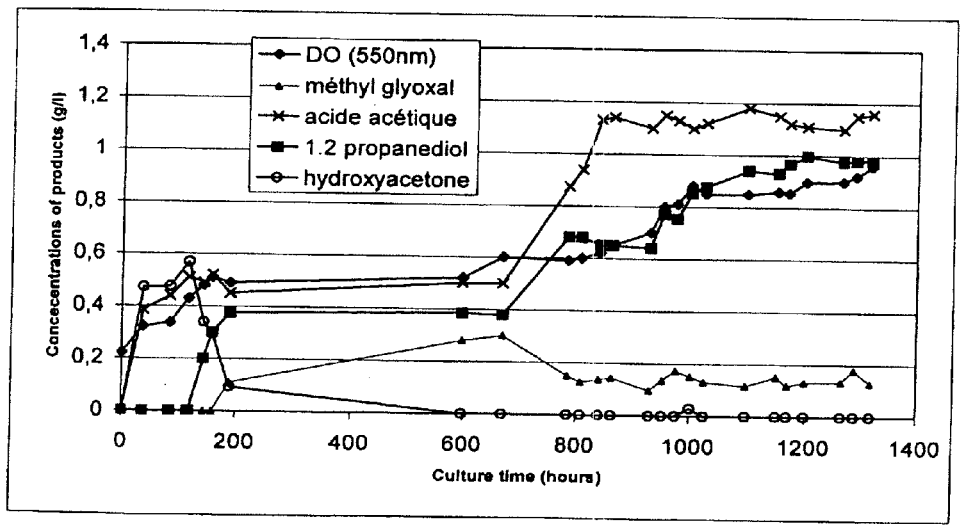

At the start of culture, the initial concentration of glucose in the culture feed tank was 20 g/l, the dilution rate was 0.04 h$^{-1}$ and a continuous nitrogen flow was maintained to ensure anaerobic conditions. The cell concentration and the production of 1,2-propanediol and acetate were low. After several weeks of culture the growth and concentrations of products increased, and a steady regimen was reached that was characterised by a residual glucose concentration and constant concentrations of products (FIG. 2).

EXAMPLE 3

Characterisation of an Evolved Pyruvate Dehydrogenase Complex with Low Sensitivity to NADH The evolution of the pyruvate dehydrogenase complex (PDHc) towards a PDHc with low sensitivity to NADH was demonstrated by an assay of the activity of the evolved enzyme in vitro, and by comparison of the sequence of one of the genes (lpd) coding for the lipoamide dehydrogenase of the evolved PDHc with that of the gene of the wild PDHc.

a) Assay of the Enzyme Activity of the Pyruvate Dehydrogenase Complex

The assay of the in vitro enzyme activity of the PDHc of the strain E. coli* MG1655 Δ tpiA, ΔpflAB, ΔadhE, ldhA::kana, ΔgloA, ΔaldA, ΔaldB was performed using the protocol described by Schwartz and Reed (Schwartz E. R. & Reed L. J. (1970) Regulation of the activity of the pyruvate dehydrogenase complex of Escherichia coli, Biochemistry, 6, 1434-1439).

An aliquot of 100 ml of cell culture was withdrawn from the chemostatic fermenter into previously degassed vials handled under an anaerobic hood. The cell suspension was centrifuged for 10 minutes at 6000 rpm. The pellet was re-suspended in about 100 ml of 50 mM potassium phosphate buffer pH7.9, 0.5 mM thiamine pyrophosphate, and centrifuged again for 10 minutes at 6000 rpm. It was washed a second time in the same conditions. The cell pellet was re-suspended in 800 µl of buffer. The cell suspension was disrupted using an ultrasonic device in four treatment cycles (30 seconds at 30%) separated by rest periods of 2 minutes on ice. The cell debris was eliminated by centrifuging for 5 minutes at 13,400 rpm. The supernatant was the crude cell-free extract. Salts present in the cell-free extract that might interfere with the enzyme assay were eliminated by running the extract through a PD10 column equilibrated with potassium phosphate buffer pH 7.9, 0.5 mM thiamine pyrophosphate. The extract was eluted with 3.5 ml of the same buffer as above. The recovered eluate was the crude cell-free extract.

Figure 3:
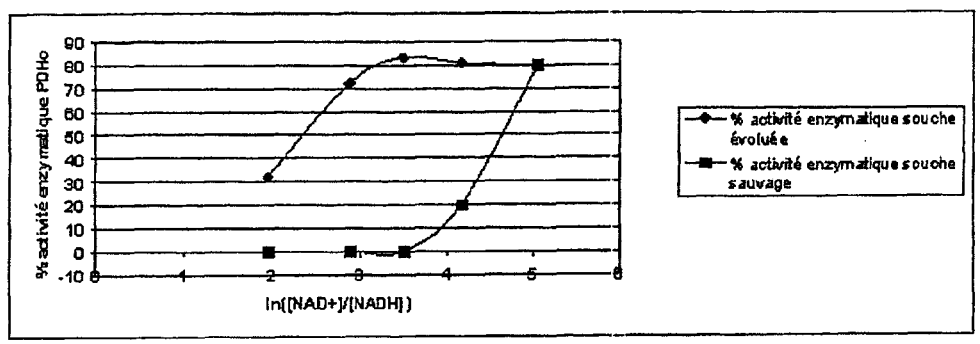
FIG. 3: Comparison of the enzyme activity of the pyruvate dehydrogenase complex of the wild strain and of the evolved strain according to the invention against increasing concentrations of NADH.

The enzyme activity of the crude cell-free extract was first measured in the absence of NADH, and then in the presence of concentrations of NADH increasing from 0.14 mM to 2.7 mM. The results obtained were compared with those reported in the literature for the wild strain of E. coli in FIG. 3 (Snoep J. L., De Graef M. R., Westphal A. H., De Kok A. Teixeira de Mattos M. J. and Neijssel O. M. (1993) Differences in sensitivity to NADH of purified pyruvate dehydrogenase complexes of Enterococcus faecalis, Lactococcus lactis, Azotobacter vinelandii and Escherichia coli: implications for their activity in vivo, FEMS Microbiology Letters, 114, 279-284).

The results obtained indicate that the PDHc of the evolved modified strain E. coli MG1655 Δ tpiA, ΔpflAB, ΔadhE, ldhA::kana, ΔgloA, ΔaldA, ΔaldB was less sensitive to NADH than the wild strain of E. coli. For a ratio [NAD+]/[NADH]≅33, total inhibition of the activity of the PDHc of the wild strain was observed, whereas 80% of the activity of the evolved PDHc was found.

b) Determination of the Sequence of the Gene lpd Coding for the Lipoamide Dehydrogenase of the Pyruvate Dehydrogenase Complex of the Evolved Strain MG1655 ΔtpiA, ΔpflAB, ΔadhE, ldhA::kana, ΔgloA, ΔaldA, ΔaldB The chromosomal DNA of the strain E. coli*MG1655 Δ tpiA, ΔpflAB, ΔadhE, ldhA::kana, ΔgloA, ΔaldA, ΔaldB was extracted from 1 ml of an overnight culture in LB. After centrifuging, the cells were washed with sterile water and disrupted by heat shock applied for 5 minutes at 94° C. The chromosomal DNA was recovered in the supernatant after centrifuging. The gene lpd (sequence 127912 to 129336) coding for the lipoamide dehydrogenase (E3) of the pyruvate dehydrogenase complex was amplified by PCR using the following two oligonucleotides:

AceEf (SEQ ID NO 27):
cgcgtgatcgacggtgctgatggtgcccg (homologous to the sequence 127504 to 127532)

YacH r (SEQ ID NO 28):
aagttcaggagagccgccc (homologous to the sequence 127513 to 129531)

A PCR product with 2000 base pairs corresponding to the gene lpd was obtained and sequenced. The results obtained show the presence of a point mutation where alanine 55 is replaced by a valine.

EXAMPLE 4

The Conversion Pathway of Methylglyoxal into 1,2-propanediol of the Evolved Modified Strain E. coli MG1655 Δ tpiA, ΔpflAB, ΔadhE, ldhA:: kana, ΔgloA, ΔaldA, ΔaldB does not Involve Glycerol Dehydrogenase To show that the improved performance of the evolved modified strain E. coli MG1655 Δ tpiA, ΔpflAB, ΔadhE, ldhA:: kana, ΔgloA, ΔaldA, ΔaldB is not due to an evolution of the glycerol dehydrogenase coded by the gene gldA, an evolved strain E. coli MG1655 Δ tpiA, ΔpflAB, ΔadhE, ldhA::kana, ΔgloA, ΔaldA, ΔaldB in which the gene gldA is deleted was engineered.

a) Construction of a Modified Strain MG1655 ΔgldA::cm

The gene gldA was inactivated as indicated in Example 1 by inserting a chloramphenicol antibiotic resistance cassette and deleting most of the genes concerned using the technique described by Datsenko, K. A. & Wanner, B. L. (2000).

Two oligonucleotides were used to carry out the deletion:
1. gldA D f, consisting of 100 bases (SEQ ID NO 29):

gttattcccactcttgcaggaaacgctgaccgtactggtcggctaccagc agagcggcgtaaacctgatctggcgtcgcgGTGTAGGCTGGAGCTGCTTC

G with:
- a region (lower case letters) homologous to the sequence (4135512 to 4135592) of the gene gldA (sequence 4135512 to 4136615), reference sequence on the website genolist.pasteur.fr/Colibri/, and
- a region (upper case letters) for the amplification of the chloramphenicol resistance cassette of the plasmid pKD3 (Datsenko, K. A. & Wanner, B. L. (2000)

2. gldA D r, consisting of 100 bases (SEQ ID NO 30):

atggaccgcattattcaatcaccgggtaaatacatccagggcgctgatgt gattaatcgtctgggcgaatacctgaagccCATATGAATATCCTCCTTAG

- a region (lower case letters) homologous to the sequence (4136535-4136615) of the gene gldA (4135512 to 4136615), and
- a region (upper case letters) for the amplification of the chloramphenicol antibiotic resistance cassette carried by the plasmid pKD3.

The oligonucleotides gldA D r and gldA D f were used to amplify the chloramphenicol resistance cassette from the plasmid pKD3. The PCR product obtained was then introduced by electroporation into the strain MG1655 (pKD46) in which the expressed enzyme Red recombinase permits homologous recombination. The antibiotic-resistant transformants were then selected and the insertion of the chloramphenicol resistance cassette was checked by PCR analysis with the oligonucleotides YijF D and TalCr.

YijF D (SEQ ID NO 31):
gcctggatttgtaccacggttggtggaacggcggg (homologous to the sequence from 4135140 to 4135174)

TalCr (SEQ ID NO 32):
cacgcatattccccattgccgggg (homologous to the sequence from 4137216 to 4137239)

A PCR product with 2100 base pairs was obtained for the wild gene and the deleted gene, and replaced by the chloramphenicol resistance gene. Thus the PCR products obtained were then digested by the SalI restriction enzyme. Two fragments of about 1000 base pairs were obtained for the wild PCR product, whereas the PCR product containing the chloramphenicol resistance gene was not digested.

b) Construction of an Evolved Modified Strain MG1655 Δ tpiA, ΔpflAB, ΔadhE, ldhA::kana, ΔgloA, ΔaldA, ΔaldB ΔgldA::cm The gene gldA of the evolved strain MG1655 ΔtpiA, ΔpflAB, ΔadhE, ldhA::kana, ΔgloA, Δ aldA ΔaldB was inactivated as in Example 1 using the phage P1 technique (see protocol c). The phage P1 lysate was obtained with the strain MG1655 ΔgldA::cm, and the transduction of the strain MG1655 ΔtpiA, ΔpflAB, ΔadhE, ldhA::kana, ΔgloA, ΔaldA was carried out using this lysate. The chloramphenicol-resistant transductants were verified using the oligonucleotides YijF D and TalCr to check the mutation of the gene gldA.

c) Culture of Evolved Modified Strains E. coli*MG 1655 Δ tpiA, ΔpflAB, ΔadhE, ldhA::kana, ΔgloA, ΔaldA, ΔaldB ΔgldA::cm and E. coli*MG 1655 Δ tpiA, ΔpflAB, ΔadhE, ldhA::kana, ΔgloA, ΔaldA, ΔaldB The two evolved modified strains E. coli*MG 1655 Δ tpiA, ΔpflAB, ΔadhE, ldhA::kana, ΔgloA, ΔaldA, ΔaldB ΔgldA::cm and E. coli*MG 1655 Δ tpiA, ΔpflAB, ΔadhE, ldhA::kana, ΔgloA, ΔaldA, ΔaldB were grown at unregulated pH in a minimum culture medium supplemented with sodium and yeast extract with an initial glucose concentration of 20 g/l in anaerobic conditions for 10 days. The profile of the fermentation products obtained shows that the deletion of the gene gldA did not cause any reduction of the production of 1,2-propanediol (Table 1).

TABLE 1

Comparison of the concentrations of substrates and fermentation products after 10 days of culture of evolved modified strains E. coli*MG 1655 ΔtpiA, ΔpflAB, ΔadhE, ldhA :: kana, ΔgloA, ΔaldA, ΔaldB ΔgldA ::cm and E. coli*MG 1655 Δ tpiA, ΔpflAB, ΔadhE, ldhA :: kana, ΔgloA, ΔaldA, ΔaldB

| Strain | Optical density | Glucose consumed (g/l) | Methyl glyoxal (g/l) | Acetic acid (g/l) | 1,2-propanediol (g/l) |
|---|---|---|---|---|---|
| E. coli*MG 1655 ΔtpiA, ΔpflAB, ΔadhE, dhA :: kana, ΔgloA, ΔaldA, ΔaldB, ΔgldA ::cm | 1.5 | 7.3 | 1.2 | 2.1 | 1.7 |
| E. coli*MG 1655 ΔtpiA, ΔpflAB, ΔadhE, dhA :: kana, ΔgloA, ΔaldA, ΔaldB | 1.9 | 9.6 | 1.4 | 1.9 | 1.2 |

EXAMPLE 5

Improvement in the Yield of the Conversion of Glucose into 1,2-propanediol by Deletion of the Gene edd Coding for 6-phospho-gluconate Dehydratase in the Evolved Strain E. coli*MG 1655 Δ tpiA, ΔpflAB, ΔadhE, ldhA::kana, ΔgloA, ΔaldA, ΔaldB.

a) Construction of a Modified Strain MG1655 Δedd::cm

The gene edd was inactivated as indicated in Example 1 by inserting a chloramphenicol antibiotic resistance cassette and deleting most of the genes concerned using the technique described by Datsenko, K. A. & Wanner, B. L. (2000).

Two oligonucleotides were used to carry out the deletion:
1. edd D f, consisting of 100 bases (SEQ ID NO 33)

ttaaaaagtgatacaggttgcgccctgttcggcaccggacagttttcac gcaaggcgctgaataattcacgtcctgttcGTGTAGGCTGGAGCTGCTTC

G with:
- a region (lower case letters) homologous to the sequence (1930817 to 4) of the gene edd (sequence 1930817 to 1932628), reference sequence on the website genolist.pasteur.fr/Colibri/, and a region (upper case letters) for the amplification of the chloramphenicol resistance cassette of the plasmid pKD3 (Datsenko, K. A. & Wanner, B. L. (2000)

2. edd D r, consisting of 100 bases (SEQ ID NO 34):

atgaatccacaattgttacgcgtaacaaatcgaatcattgaacgttcgcg cgagactcgctctgcttatctcgcccggatCATATGAATATCCTCCTTAG a region (lower case letters) homologous to the sequence (1932548-1932628) of the gene edd (sequence 1930817 to 1932628), and a region (upper case letters) for the amplification of the chloramphenicol antibiotic resistance cassette carried by the plasmid pKD3.

The oligonucleotides edd D r and edd D f are used to amplify the chloramphenicol antibiotic resistance cassette from the plasmid pKD3. The PCR product obtained was introduced by electroporation into the strain MG1655 (pKD46) in which the expressed enzyme Red recombinase permits homologous recombination. The antibiotic-resistant transformants were then selected and the insertion of the resistance cassette was then checked by PCR analysis using the oligonucleotides eda d and zwf r:

Eda d (SEQ ID NO 35):
CCCCGGMTCAGAGGMTAGTCCC (homologous to the sequence from 1930439 to 1930462)

Zwf r (SEQ ID NO 36):
GGGTAGACTCCATTACTGAGGCGTGGGCG (homologous to the sequence from 1932968 to 1932996)

b) Construction of an Evolved Modified Strain MG1655 Δ tpiA, ΔpflAB, ΔadhE, ldhA::kana, ΔgloA, ΔaldA, ΔaldB Δedd::cm The gene edd in the evolved strain MG1655 ΔtpiA, ΔpflAB, ΔadhE, ldhA::kana, ΔgloA, Δ aldA, ΔaldB was inactivated as in Example 1 using the phage P1 technique (see protocol c). The phage P1 lysate was obtained with the strain MG1655 Δedd::cm, and the transduction of the strain MG1655 ΔtpiA, ΔpflAB, ΔadhE, ldhA::kana, ΔgloA, ΔaldA, ΔaldB was carried out using this lysate. The chloramphenicol-resistant transductants were verified using the oligonucleotides eda d and zwf r to verify the mutation of the gene edd.

c) Culture of Evolved Modified Strains E. coli*MG 1655 Δ tpiA, ΔpflAB, ΔadhE, ldhA::kana, ΔgloA, ΔaldA, ΔaldB, Δedd::cm and E. coli*MG 1655 Δ tpiA, ΔpflAB, ΔadhE, ldhA::kana, ΔgloA, ΔaldA, ΔaldB The two evolved modified strains E. coli*MG 1655 Δ tpiA, ΔpflAB, ΔadhE, ldhA::kana, ΔgloA, ΔaldA, ΔaldB, Δedd::cm and E. coli*MG 1655 Δ tpiA, ΔpflAB, ΔadhE, ldhA::kana, ΔgloA, ΔaldA, ΔaldB were grown at unregulated pH in a minimum culture medium supplemented with sodium nitrate and yeast extract with an initial glucose concentration of 20 g/l in anaerobic conditions for 10 days. The profile of the fermentation products obtained shows that the deletion of the gene edd induced an increase in the yield of the conversion of glucose into 1,2-propanediol of 0.13 g/g to 0.35 g/g (Table 2). The deletion of the gene edd in the evolved strain E. coli*MG 1655 Δ tpiA, ΔpflAB, ΔadhE, ldhA::kana, ΔgloA, ΔaldA, ΔaldB thus improved the performance of the strain.

TABLE 2

Comparison of concentrations of substrate and fermentation products after 10 days culture of evolved modified strains E. coli*MG 1655 Δ tpiA, ΔpflAB, ΔadhE, ldhA :: kana, ΔgloA, ΔaldA, ΔaldB Δedd ::cm and E. coli*MG 1655 Δ tpiA, ΔpflAB, ΔadhE, ldhA :: kana, ΔgloA, ΔaldA, ΔaldB

| Strain | Optical density | Glucose consumed (g/l) | Methyl glyoxal (g/l) | Acetic acid (g/l) | 1,2-propanediol (g/l) | Y 1,2-pdiol/glucose (g/g) |
|---|---|---|---|---|---|---|
| E. coli* ΔtpiA, ΔpflAB, ΔadhE, dhA :: kana, ΔgloA, ΔaldA, ΔaldB, Δedd ::cm | 1.2 | 5 | 0.2 | 1.5 | 1.8 | 0.35 |
| E. coli* ΔtpiA, ΔpflAB, ΔadhE, dhA :: kana, ΔgloA, ΔaldA, ΔaldB | 1.9 | 9.6 | 1.4 | 1.9 | 1.2 | 0.13 |

EXAMPLE 6

Construction of a Modified Strain E. coli MG1655 Δ tpiA, ΔpflAB, ΔadhE, ldhA::kana, ΔgloA, ΔaldA, ΔaldB, Δedd::cm (pSOS95T) able to Produce 1,2-propanediol and Acetone The plasmid named pSOS95T is a shuttle expression vector for E. coli/C. acetobutylicum bearing the acetone operon of Clostridium acetobutylicum made up of four genes adc, cffA, B, thl coding respectively for acetoacetate carboxylase, coenzyme A transferase and thiolase under the dependence of the thiolase promoter. These three enzymes catalyse the conversion of acetyl-CoA and acetate into acetone and carbon dioxide. The plasmid pSOS95T was obtained by insertion in the plasmid pSOS95 (Gene bank accession number AY187686) of the gene thl of C. acetobutylicum coding for thiolase, at the site BamH1 located between the thiolase promoter and the gene cffA. The plasmid pSOS95T was introduced into the evolved strain E. coli* MG1655 Δ tpiA, ΔpflAB, ΔadhE, ldhA::kana, ΔgloA, ΔaldA, ΔaldB, Δedd::cm by electroporation.

Electrocompetent cells of the strain E. coli*MG1655 Δ tpiA, ΔpflAB, ΔadhE, ldhA:: kana, ΔgloA, ΔaldA, ΔaldB, Δedd::cm were prepared from an overnight culture of the strain in LB. A culture of 10 ml LB in a conical flask was seeded (1/100) with the overnight culture and incubated at 37° C. When the optical density of the culture at 550 nm reached a value between 0.4 and 0.6, 1 ml of culture was taken and centrifuged. The cells were washed with water and with a 10% solution of glycerol, before being re-suspended in 0.05 ml of a 10%. solution of glycerol. The cells were electroporated immediately (25 μF, 200 Ω, 2.5 kV) (Gene Pulser, Biorad) with 5 μl of the plasmid preparation pSOS95T (Qiagen, Hilden, Germany). After 1 hour of phenotypic expression in SOC medium (Sambrook J., Fristch E. F. & Maniatis T. (1989) Molecular Cloning: a Laboratory Manual, 2nd ed Cold Spring Harbor Laboratory, Cold Spring Harbor, N.Y.) at 37° C., the transformants were selected on agar medium with 100 μg/ml carbenicillin at 37° C.

The transformants were returned to liquid culture in the presence of carbenicillin overnight to carry out an extraction of plasmid DNA (Qiagen, Hilden Germany) to check for the presence of the plasmid pSOS95T and make sure it was satisfactory by enzymatic digestion.

EXAMPLE 7

Culture of the Evolved Modified Strain E. coli*MG1655 Δ tpiA, ΔpflAB, ΔadhE, ldhA::kana, ΔgloA, ΔaldA, ΔaldB, Δedd::cm (pSOS95T) Able to Produce 1,2-propanediol and Acetone The evolved modified strain E. coli* MG1655 Δ tpiA, ΔpflAB, ΔadhE, ldhA::kana, ΔgloA, ΔaldA, ΔaldB Δedd::cm (pSOS95T) was grown at unregulated pH in a minimum culture medium supplemented with sodium nitrate and yeast extract with an initial glucose concentration of 20 g/l in anaerobic conditions (Table 3). The assay of fermentation products showed that the evolved strain E. coli* MG1655 ΔtpiA, ΔpflAB, ΔadhE, ldhA::kana, ΔgloA, ΔaldA, ΔaldB Δedd::cm (pSOS95T) produced a mixture of 1,2-propanediol, acetate and acetone.

TABLE 3

Comparison of concentrations of substrate and fermentation products after 10 days culture of the evolved modified strain E. coli*MG 1655 ΔtpiA, ΔpflAB, ΔadhE, ldhA :: kana, ΔgloA, ΔaldA, ΔaldB, Δedd ::cm and E. coli*MG 1655 ΔtpiA, ΔpflAB, ΔadhE, ldhA :: kana, ΔgloA, ΔaldA, ΔaldB, Δedd :: cm

| Strain | Optical density | Glucose consumed (g/l) | Methyl glyoxal (g/l) | Acetic acid (g/l) | 1,2-propanediol (g/l) | Acetone (g/l) |
|---|---|---|---|---|---|---|
| E. coli* ΔtpiA, ΔpflAB, ΔadhE, dhA :: kana, ΔgloA, ΔaldA, ΔaldB, Δedd :: cm (pSOS95T) | 1.4 | 4.8 | 0.3 | 1.3 | 1.6 | 0.1 |
| E. coli* ΔtpiA, ΔpflAB, ΔadhE, ldhA :: kana, ΔgloA, ΔaldA, ΔaldB, Δedd :: cm | 1.2 | 5 | 0.2 | 1.5 | 1.8 | / |

REFERENCES

V Altaras N. E. and Cameron D. (1999) Metabolic engineering of a 1,2-propanediol pathway in Escherichia coli: Appl. Env. Microb., 65, 1180-1185.

Altaras N. E. and Cameron D. C. (2000) Enhanced production of (R) 1,2-propanediol by metabolically engineered Escherichia coli: Biotechnol. Prog. 16, 940-946

Altaras N E, Etzel M R and Cameron D C. (2001) Conversion of sugars to 1,2-propanediol by Thermoanaerobacterium thermosaccharolyticum HG-8: Biotechnol. Prog. 17, 52-56

Bunch P. K., Mat-Jan F. and Clark D. P. (1997) The ldhA gene encoding the fermentative lactate dehydrogenase of Escherichia coli: microbiology, 143, 187-195.

Cameron D. C., Altaras N. E., Hoffman M. L. and Shaw A. J. (1998) Metabolic engineering of propanediol pathways: Biotechnol. Prog., 14, 116-125.

Cameron D. C., Shaw A. J. and Altaras N. E. (1998) Microbial production of 1,2-propanediol from sugar WO 98/37204

Cameron D. C., Shaw A. J. and Altaras N. E. (2000) Microbial production of 1,2-propanediol from sugar U.S. Pat. No. 6,087,140

Cameron D. C., Shaw A. J. and Altaras N. E. (2001) Microbial production of 1,2-propanediol from sugar U.S. Pat. No. 6,303,352

Carrier T A and Keasling J. D. (1999) Library of synthetic 5' secondary structures to manipulate mRNA stability in Escherichia coli, Biotechnol. prog., 15, 58-64

Cheperanov P. P. and Wackernagel W. (1995) Gene disruption in Escherichia coli: $Tc^R$ and $Km^R$ cassettes with option of Flp-catalyzed excision of the antibiotic-resistance determinant, gene, 158, 9-14

Datsenko, K. A. and Wanner, B. L. (2000) One-step inactivation of chromosomal genes in Escherichia coli K-12 using PCR products. Proc. Natl. Acad. Sci. USA 97: 6640-6645

Sambrook J., Fristch E. F. and Maniatis T. (1989) Molecular Cloning: a Laboratory Manual, 2nd ed. Cold Spring Harbor Laboratory, Cold Spring Harbor, N.Y.

Schwartz E. R. and Reed L. J. (1970) Regulation of the activity of the pyruvate dehydrogenase complex of Escherichia coli Biochemistry, 6, 1434-1439

Snoep J. L., De Graef M. R., Westphal A. H., De Kok A. Teixeira de Mattos M. J. and Neijssel O. M. (1993) Differences in sensitivity to NADH of purified pyruvate dehydrogenase complexes of Enterococcus faecalis, Lactococcus lactis, Azotobacter vinelandii and Escherichia coli: implications for their activity in vivo, FEMS microbiology letters, 114, 279-284)).

Tran Din K. and Gottschalk G. (1985) Formation of D(−)-1, 2-propanediol and D(−)-lactate from glucose by Clostridium sphenoides under phosphate limitation: Arch. Microbiol. 142, 87-92.

The invention claimed is:

1. A method for the preparation of a strain of evolved *E. coli* for the production of 1,2-propanediol by the metabolism of a simple carbon source, said method comprising:
   (a) providing an initial *E. coli* strain comprising deletion of tpiA gene and deletion of at least one gene involved in the conversion of methylglyoxal (propanal) into lactate;
   (b) culturing the initial *E. coli* strain, under selection pressure in an appropriate growth medium comprising a simple carbon source for a time period sufficient to allow an increase in growth;
   (c) causing evolution, in said *E. coli* strain, of one or more genes involved in the biosynthesis pathway from DHAP to methylglyoxal and then to 1,2-propanediol towards evolved genes having an improved 1,2-propanediol synthase activity by applying increasing rates of dilution in such a way as to conserve in the growth medium only those *E. coli* strain that display a growth rate equal to or higher than the imposed rate of dilution, to provide an evolved strain; and
   (d) selecting and isolating the evolved *E. coli* strain having an improved 1,2-propanediol synthase activity,
   wherein the initial *E. coli* strain comprises deletion of genes gloA, aldA, and aldB.

2. A method for the preparation of a strain of evolved *E. coli* for the production of 1,2-propanediol by the metabolism of a simple carbon source said method comprising:
   (a) providing an initial *E. coli* strain comprising deletion of tpiA gene and deletion of at least one gene involved in the conversion of methylglyoxal (propanal) into lactate;
   (b) culturing the initial *E. coli* strain, under selection pressure in an appropriate growth medium comprising a simple carbon source for a time period sufficient to allow an increase in growth;
   (c) causing evolution, in said *E. coli* strain, of one or more genes involved in the biosynthesis pathway from DHAP to methylglyoxal and then to 1,2-propanediol towards evolved genes having an improved 1,2-propanediol synthase activity by applying increasing rates of dilution in such a way as to conserve in the growth medium only those *E. coli* strain that display a growth rate equal to or higher than the imposed rate of dilution, to provide an evolved strain; and
   (d) selecting and isolating the evolved *E. coli* strain having an improved 1,2-propanediol synthase activity,
   wherein the initial *E. coli* strain comprises deletion of genes ldhA, pflA, pflB, adhE and edd.

3. The method of claim 1, wherein the initial *E. coli* strain further comprises a pyruvate dehydrogenase complex.

4. The method of claim 3, wherein the pyruvate dehydrogenase complex has low sensitivity to inhibition by NADH.

5. The method of claim 3, wherein the pyruvate dehydrogenase complex is endogenous.

6. The method of claim 1, wherein one or more heterologous genes adc, ctfAB, and thl are introduced into the evolved *E. coli* microorganisms to provide a modified evolved *E. coli* strain.

7. The method of claim 6, wherein the one or more heterologous genes adc ctfAB, and thl are from *C. acetobutylicum*.

8. The method of claim 6, wherein the modified evolved *E. coli* strain comprising one or more heterologous genes adc, ctfAB, and thl are grown under selection pressure in an appropriate growth medium comprising a simple carbon source in order to cause, in said modified evolved *E. coli* strain, the evolution of one or more genes involved in the conversion of acetyl-CoA and acetate to acetone towards an improved acetone synthase activity, the second generation of resulting evolved microorganisms having an improved 1,2-propanediol synthase activity and an improved acetone synthase activity are then selected and isolated.

9. An evolved *E. coli* strain obtained by the method according to claim 1, wherein said evolved *E. coli* strain comprises a pyruvate dehydrogenase complex, and wherein said evolved *E. coli* strain compromises an lpd gene encoding a lipoamide dehydrogenase of the pyruvate dehydrogenase complex, and wherein the lpd gene has a point mutation whereby alanine 55 is replaced by valine.

10. An *E. coli* strain comprising deletion of the gene tpiA, deletion of at least one gene involved in the conversion of methylglyoxal into lactate, and deletion of the genes ldhA, pflA, pflB, adhE and edd.

11. The strain of claim 10, wherein the gene involved in the conversion of methylglyoxal into lactate is selected among the group consisting of gloA, aldA and aldB.

12. The strain of claim 11, wherein the *E. coli* strain comprises deletion of the genes gloA, aldA, and aldB.

13. The strain of claim 10, wherein the initial *E. coli* strain also contains a pyruvate dehydrogenase complex.

14. The strain of claim 13, wherein the pyruvate dehydrogenase complex has low sensitivity to inhibition by NADH.

* * * * *

SEQUENCE LISTING

<160> NUMBER OF SEQ ID NOS: 36

<210> SEQ ID NO 1
<211> LENGTH: 102
<212> TYPE: DNA
<213> ORGANISM: artificial sequence
<220> FEATURE:
<223> OTHER INFORMATION: Other information : synthetic oligonucleotide

<400> SEQUENCE: 1
atgcgacatc ctttagtgat gggtaactgg aaactgaacg gcagccgcca catggttcac    60
gagctggttt ctaacctgcg tacatatgaa tatcctcctt ag    102

<210> SEQ ID NO 2
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 2
cttaagcctg tttagccgct tctgcagctt taacgattac tgcgaaggcg tcagctttca    60
gagaagcacc accaaccagc tgtaggctgg agctgcttcg    100

<210> SEQ ID NO 3
<211> LENGTH: 20
<212> TYPE: DNA
<213> ORGANISM: artificial sequence
<220> FEATURE:
<223> OTHER INFORMATION: Other information : synthetic oligonucleotide

<400> SEQUENCE: 3
ggtgatgata gttatcgccg    20

<210> SEQ ID NO 4
<211> LENGTH: 20
<212> TYPE: DNA
<213> ORGANISM: artificial sequence
<220> FEATURE:
<223> OTHER INFORMATION: Other information : synthetic oligonucleotide

<400> SEQUENCE: 4
cgtgccatcg acagcagtcc    20

<210> SEQ ID NO 5
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 5
ccggacatcc tgcgttgccg taaatctggt gttctgaccg gtctgccaga tgcatatggc    60
cgtggccgta tcatcggtga catatgaata tcctccttag    100

<210> SEQ ID NO 6
<211> LENGTH: 94
<212> TYPE: DNA
<213> ORGANISM: artificial sequence
<220> FEATURE:
<223> OTHER INFORMATION: Other information : synthetic oligonucleotide

<400> SEQUENCE: 6

```
gatgcactat aagatgtgtt aaaaacgctg tagcagaatg aagcgcggaa taaaaaagcg      60
gcaactcaat aaagttgccg ctggagctgc ttcg                                  94
```

<210> SEQ ID NO 7
<211> LENGTH: 30
<212> TYPE: DNA
<213> ORGANISM: artificial sequence
<220> FEATURE:
<223> OTHER INFORMATION: Other information : synthetic oligonucleotide

<400> SEQUENCE: 7

```
agacattaaa aatatacgtg cagctacccg                                       30
```

<210> SEQ ID NO 8
<211> LENGTH: 30
<212> TYPE: DNA
<213> ORGANISM: artificial sequence
<220> FEATURE:
<223> OTHER INFORMATION: Other information : synthetic oligonucleotide

<400> SEQUENCE: 8

```
gtgaaagctg acaacccttt tgatctttta                                       30
```

<210> SEQ ID NO 9
<211> LENGTH: 101
<212> TYPE: DNA
<213> ORGANISM: artificial sequence
<220> FEATURE:
<223> OTHER INFORMATION: Other information : synthetic oligonucleotide

<400> SEQUENCE: 9

```
atggctgtta ctaatgtcgc tgaacttaac gcactcgtag agcgtgtaaa aaaagcccag      60
cgtgaatatg ccagtttcac tcatatgaat atcctcctta g                         101
```

<210> SEQ ID NO 10
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 10

```
caataacgaa tgatagcaat tttaagtagt taggaggtga aaaatgctgt caaaaggcgt      60
attgtcagcg cgtcttttca tgtaggctgg agctgcttcg                           100
```

<210> SEQ ID NO 11
<211> LENGTH: 22
<212> TYPE: DNA
<213> ORGANISM: artificial sequence
<220> FEATURE:
<223> OTHER INFORMATION: Other information : synthetic oligonucleotide

<400> SEQUENCE: 11

```
ggctcattgc accaccatcc ag                                               22
```

<210> SEQ ID NO 12
<211> LENGTH: 24
<212> TYPE: DNA
<213> ORGANISM: artificial sequence
<220> FEATURE:
<223> OTHER INFORMATION: Other information : synthetic oligonucleotide

<400> SEQUENCE: 12

```
gaaaagacgc gctgacaata cgcc                                             24
```

<210> SEQ ID NO 13
<211> LENGTH: 20
<212> TYPE: DNA
<213> ORGANISM: artificial sequence
<220> FEATURE:
<223> OTHER INFORMATION: Other information : synthetic oligonucleotide

<400> SEQUENCE: 13
gccatcagca ggcttagccg                                                    20

<210> SEQ ID NO 14
<211> LENGTH: 23
<212> TYPE: DNA
<213> ORGANISM: artificial sequence
<220> FEATURE:
<223> OTHER INFORMATION: Other information : synthetic oligonucleotide

<400> SEQUENCE: 14
gggtattgtg gcatgtttaa ccg                                                23

<210> SEQ ID NO 15
<211> LENGTH: 101
<212> TYPE: DNA
<213> ORGANISM: artificial sequence
<220> FEATURE:
<223> OTHER INFORMATION: Other information : synthetic oligonucleotide

<400> SEQUENCE: 15
atgcgtcttc ttcataccat gctgcgcgtt ggcgatttgc aacgctccat cgatttttat        60
accaaagtgc tgggcatgaa gtgtaggctg gagctgcttc g                           101

<210> SEQ ID NO 16
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 16
ttagttgccc agaccgcgac cggcgtcttt ctcttcgatt aactcaattt tgtaaccgtc        60
cggatcttcc acaaacgcga catatgaata tcctccttag                             100

<210> SEQ ID NO 17
<211> LENGTH: 31
<212> TYPE: DNA
<213> ORGANISM: artificial sequence
<220> FEATURE:
<223> OTHER INFORMATION: Other information : synthetic oligonucleotide

<400> SEQUENCE: 17
gaagtggtcg atgccgggat tgaagaatgg g                                       31

<210> SEQ ID NO 18
<211> LENGTH: 31
<212> TYPE: DNA
<213> ORGANISM: artificial sequence
<220> FEATURE:
<223> OTHER INFORMATION: Other information : synthetic oligonucleotide

<400> SEQUENCE: 18
gggttacgtt tcagtgaggc gcgttctgcg g                                       31

<210> SEQ ID NO 19
<211> LENGTH: 102
<212> TYPE: DNA

<213> ORGANISM: artificial sequence
<220> FEATURE:
<223> OTHER INFORMATION: Other information : synthetic oligonucleotide

<400> SEQUENCE: 19
atgtcagtac cgttcaaca tcctatgtat atcgatggac agtttgttac ctggcgtgga    60
gacgcatgga ttgatgtggt agtgtaggct ggagctgctt cg    102

<210> SEQ ID NO 20
<211> LENGTH: 101
<212> TYPE: DNA
<213> ORGANISM: artificial sequence
<220> FEATURE:
<223> OTHER INFORMATION: Other information : synthetic oligonucleotide

<400> SEQUENCE: 20
ttaagactgt aaataaacca cctgggtctg cagatattca tgcaagccat gtttaccatc    60
tgcgccgcca ataccggatt tcatatgaat atcctcctta g    101

<210> SEQ ID NO 21
<211> LENGTH: 31
<212> TYPE: DNA
<213> ORGANISM: artificial sequence
<220> FEATURE:
<223> OTHER INFORMATION: Other information : synthetic oligonucleotide

<400> SEQUENCE: 21
tgcagcggcg cacgatggcg acgttccgcc g    31

<210> SEQ ID NO 22
<211> LENGTH: 31
<212> TYPE: DNA
<213> ORGANISM: artificial sequence
<220> FEATURE:
<223> OTHER INFORMATION: Other information : synthetic oligonucleotide

<400> SEQUENCE: 22
cacgatgacg accattcatg cctatactgg c    31

<210> SEQ ID NO 23
<211> LENGTH: 101
<212> TYPE: DNA
<213> ORGANISM: artificial sequence
<220> FEATURE:
<223> OTHER INFORMATION: Other information : synthetic oligonucleotide

<400> SEQUENCE: 23
tcagaacagc cccaacggtt tatccgagta gctcaccagc aggcacttgg tttgctggta    60
atgctccagc atcatcttgt gtgtaggctg gagctgcttc g    101

<210> SEQ ID NO 24
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 24
atgaccaata atcccccttc agcacagatt aagcccggcg agtatggttt ccccctcaag    60
ttaaaagccc gctatgacaa catatgaata tcctccttag    100

<210> SEQ ID NO 25
<211> LENGTH: 40
<212> TYPE: DNA

```
<213> ORGANISM: artificial sequence
<220> FEATURE:
<223> OTHER INFORMATION: Other information : synthetic oligonucleotide

<400> SEQUENCE: 25
catatttccc tcaaagaata taaaaaagaa caattaacgc                                  40

<210> SEQ ID NO 26
<211> LENGTH: 31
<212> TYPE: DNA
<213> ORGANISM: artificial sequence
<220> FEATURE:
<223> OTHER INFORMATION: Other information : synthetic oligonucleotide

<400> SEQUENCE: 26
tatgttcatg cgatggcgca ccagctgggc g                                           31

<210> SEQ ID NO 27
<211> LENGTH: 29
<212> TYPE: DNA
<213> ORGANISM: artificial sequence
<220> FEATURE:
<223> OTHER INFORMATION: Other information : synthetic oligonucleotide

<400> SEQUENCE: 27
cgcgtgatcg acggtgctga tggtgcccg                                              29

<210> SEQ ID NO 28
<211> LENGTH: 19
<212> TYPE: DNA
<213> ORGANISM: artificial sequence
<220> FEATURE:
<223> OTHER INFORMATION: Other information : synthetic oligonucleotide

<400> SEQUENCE: 28
aagttcagga gagccgccc                                                         19

<210> SEQ ID NO 29
<211> LENGTH: 101
<212> TYPE: DNA
<213> ORGANISM: artificial sequence
<220> FEATURE:
<223> OTHER INFORMATION: Other information : synthetic oligonucleotide

<400> SEQUENCE: 29
gttattccca ctcttgcagg aaacgctgac cgtactggtc ggctaccagc agagcggcgt            60
aaacctgatc tggcgtcgcg gtgtaggctg gagctgcttc g                               101

<210> SEQ ID NO 30
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 30
atggaccgca ttattcaatc accgggtaaa tacatccagg gcgctgatgt gattaatcgt            60
ctgggcgaat acctgaagcc catatgaata tcctccttag                                 100

<210> SEQ ID NO 31
<211> LENGTH: 35
<212> TYPE: DNA
<213> ORGANISM: artificial sequence
<220> FEATURE:
<223> OTHER INFORMATION: Other information : synthetic oligonucleotide
```

```
<400> SEQUENCE: 31
gcctggattt gtaccacggt tggtggaacg gcggg                              35

<210> SEQ ID NO 32
<211> LENGTH: 24
<212> TYPE: DNA
<213> ORGANISM: artificial sequence
<220> FEATURE:
<223> OTHER INFORMATION: Other information : synthetic oligonucleotide

<400> SEQUENCE: 32
cacgcatatt ccccattgcc gggg                                         24

<210> SEQ ID NO 33
<211> LENGTH: 101
<212> TYPE: DNA
<213> ORGANISM: artificial sequence
<220> FEATURE:
<223> OTHER INFORMATION: Other information : synthetic oligonucleotide

<400> SEQUENCE: 33
ttaaaaagtg atacaggttg cgccctgttc ggcaccggac agttttcac gcaaggcgct   60 gaataattca cgtcctgttc gtgtaggctg gagctgcttc g                     101

<210> SEQ ID NO 34
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 34
atgaatccac aattgttacg cgtaacaaat cgaatcattg aacgttcgcg cgagactcgc   60
tctgcttatc tcgcccggat catatgaata tcctccttag                        100

<210> SEQ ID NO 35
<211> LENGTH: 24
<212> TYPE: DNA
<213> ORGANISM: artificial sequence
<220> FEATURE:
<223> OTHER INFORMATION: Other information : synthetic oligonucleotide

<400> SEQUENCE: 35
ccccggaatc agaggaatag tccc                                         24

<210> SEQ ID NO 36
<211> LENGTH: 29
<212> TYPE: DNA
<213> ORGANISM: artificial sequence
<220> FEATURE:
<223> OTHER INFORMATION: Other information : synthetic oligonucleotide

<400> SEQUENCE: 36
gggtagactc cattactgag gcgtgggcg                                    29
```